United States Patent
Neyer et al.

(10) Patent No.: US 7,645,388 B2
(45) Date of Patent: Jan. 12, 2010

(54) FLOW RATE CONTROL

(75) Inventors: David W. Neyer, Castro Valley, CA (US); David J. Rakestraw, Livermore, CA (US); Jason E. Rehm, Alameda, CA (US)

(73) Assignee: Eksigent Technologies, LLC, Dublin, CA (US)

( * ) Notice: Subject to any disclaimer, the term of this patent is extended or adjusted under 35 U.S.C. 154(b) by 790 days.

(21) Appl. No.: 10/557,924

(22) PCT Filed: May 19, 2004

(86) PCT No.: PCT/US2004/015838

§ 371 (c)(1),
(2), (4) Date: Nov. 17, 2005

(87) PCT Pub. No.: WO2004/112960

PCT Pub. Date: Dec. 29, 2004

(65) Prior Publication Data

US 2007/0037293 A1 Feb. 15, 2007

Related U.S. Application Data

(63) Continuation-in-part of application No. 10/441,640, filed on May 20, 2003, now Pat. No. 6,962,658.

(51) Int. Cl.
*B01D 15/08* (2006.01)

(52) U.S. Cl. .............. 210/656; 210/101; 210/143; 210/198.2

(58) Field of Classification Search ............... 210/635, 210/656, 659, 101, 143, 198.2; 422/70; 436/161
See application file for complete search history.

(56) References Cited

U.S. PATENT DOCUMENTS

| | | | |
|---|---|---|---|
| 4,016,074 A * | 4/1977 | Porter | 210/659 |
| 4,032,445 A | 6/1977 | Munk | |
| 4,217,233 A * | 8/1980 | Michaelis | 508/299 |
| 4,239,623 A | 12/1980 | Schrenker | |
| 4,676,897 A * | 6/1987 | Kuze et al. | 204/604 |
| 4,699,718 A | 10/1987 | Jones et al. | |
| 4,728,434 A | 3/1988 | Trafford | |
| 4,849,110 A * | 7/1989 | Takata et al. | 210/656 |
| 4,859,342 A * | 8/1989 | Shirasawa et al. | 210/656 |
| 4,882,781 A * | 11/1989 | Allington | 700/282 |
| 4,917,575 A | 4/1990 | Miller, Jr. et al. | |

(Continued)

OTHER PUBLICATIONS

R.T. De Carvalho et al., "Slow-flow measurements and fluid dynamics analysis using the Fresnel drag effect," Applied Optics, (1994), pp. 6073-6077, vol. 33, No. 25.

(Continued)

*Primary Examiner*—Ernest G Therkorn
(74) *Attorney, Agent, or Firm*—Sheldon Mak Rose & Anderson PC; Jeffrey G. Sheldon

(57) ABSTRACT

A liquid sample is prepared at a preparation site and then processed, e.g. in an HPLC column. The sample is prepared and conveyed to the device at a flow rate which is substantially less than the flow rate through the device. The different flow rates are preferably provided by variable rate working fluid supplies which drive the sample from the preparation site and through the device.

7 Claims, 2 Drawing Sheets

U.S. PATENT DOCUMENTS

| | | | |
|---|---|---|---|
| 5,089,126 | A | 2/1992 | Silebi et al. |
| 5,236,847 | A * | 8/1993 | Satake et al. .................. 436/89 |
| 5,389,221 | A | 2/1995 | Jorgenson et al. |
| 5,711,786 | A | 1/1998 | Hinshaw |
| 5,738,783 | A * | 4/1998 | Shirota et al. ............ 210/198.2 |
| 5,789,258 | A | 8/1998 | Drinkwine et al. |
| 5,827,426 | A | 10/1998 | Fujii et al. |
| 5,919,368 | A * | 7/1999 | Quinn et al. ................. 210/635 |
| 5,942,093 | A | 8/1999 | Rakestraw .................. 204/450 |
| 6,063,283 | A * | 5/2000 | Shirota et al. ............... 210/656 |
| 6,290,909 | B1 | 9/2001 | Paul et al. ..................... 422/70 |
| 6,386,050 | B1 | 5/2002 | Yin et al. |
| 6,404,193 | B1 | 6/2002 | Dourdeville |
| 6,408,878 | B2 | 6/2002 | Unger et al. |
| 6,492,184 | B1 | 12/2002 | Petro et al. |
| 6,833,068 | B2 | 12/2004 | Paul et al. |
| 6,962,658 | B2 | 11/2005 | Neyer et al. |
| 2002/0017484 | A1 | 2/2002 | Dourdeville |
| 2002/0146840 | A1 | 10/2002 | Hage et al. |
| 2002/0170342 | A1 | 11/2002 | Paul et al. |
| 2002/0176804 | A1 | 11/2002 | Strand et al. |
| 2002/0189947 | A1 | 12/2002 | Paul et al. |
| 2002/0194909 | A1 | 12/2002 | Hasslebrink |
| 2002/0195344 | A1 | 12/2002 | Neyer et al. |
| 2003/0000291 | A1 | 1/2003 | Kolosov et al. |
| 2003/0019833 | A1 | 1/2003 | Unger et al. |
| 2003/0052007 | A1 | 3/2003 | Paul et al. |
| 2003/0064008 | A1 | 4/2003 | Hage et al. |
| 2003/0215855 | A1 | 11/2003 | Dubrow et al. |
| 2005/0252840 | A1 | 11/2005 | Arnold et al. |

OTHER PUBLICATIONS

P. Enoksson et al., "A Silicon Resonant Sensor Structure for Coriolis Mass-Flow Measurements," Journal of Microelectromechanical Systems, (1997), pp. 119-125, vol. 6, No. 2.

Office Action for Indian Patent Application No. 3459/CHENP/2005 mailed Mar. 14, 2007, 2 pages.

Office Action for Indian Patent Application No. 3459/CHENP/2005 mailed Mar. 3, 2008, 2 pages.

Vissers, "Recent Developments in Microcolumn Liquid Chromatography", J. of Chrom A, 856, p. 117 (1999).

Vissers et al, Optimized Injection Techniques for Micro and Capillary Liquid Chromatography, J. of Chrom A, 746, p. 1 (1996).

Bakalyar et al, "Choosing Sample Volume to Achieve Maximum Detection Sensitivity . . ." J. of Chrom A, 762, p. 167 (1997).

Foster et al., "Performance of Experimental Sample Injectors for High Performance Liquid Chromatography Microcolumns", J. of Chrom A, 869, p. 231 (2000).

McCuffin et al., "Nanoiter Injection System for Microcolumn . . .", Anal. Chem, 55, p. 580 (1983).

Alexander J.N et al., "Evaluation of Automated Isocratic . . ." Anal. Chem, 71, p. 2398 (1999).

Berry, V. et al., "Review of microliter (nanoliter) Injection . . .", Liquid Chromatography, 10, p. 3257 (1987).

Foster, Marc D., "Performance of Experimental Sample Injectors . . .", Journal of Chromatography (2000), and pp. 231-241.

International Search Report and Written Opinion of the International Searching Authority for International Patent Application No. PCT/US 04/15838.

Notice of Allowance for U.S. Appl. No. 10/441,640, mailed Mar. 11, 2005, 9 pages.

Office Action for U.S. Appl. No. 11/171,854, mailed Mar. 21, 2008, 16 pages.

* cited by examiner

US 7,645,388 B2

FLOW RATE CONTROL

CROSS REFERENCE TO RELATED APPLICATIONS

This application is 371 of PCT/US04/15835, filed May 19, 2004 and is a continuation-in-part of U.S. patent application Ser. No. 10/441,640, filed May 20, 2003 now U.S. Pat. No. 6,962,658. It is also related to commonly assigned U.S. application Ser. No. 10/246,284, filed Sep. 17, 2002, US Publication No. 2003/0052007 (now U.S. Pat. No. 7,465,382), which is a continuation-in-part of copending, commonly assigned U.S. application Ser. No. 10/155,474, filed May 24, 2002, US Publication No. 2002/01953444, which is a continuation-in-part of copending; commonly assigned U.S. application Ser. No. 09/942,884, filed Aug. 29, 2001, US Publication No. 2002/0189947, which claims the benefit of U.S. Provisional Application No. 60/298,147, filed Jun. 13, 2001. The entire disclosure of each of those applications is incorporated herein by reference for all purposes.

BACKGROUND

The invention relates to controlling the rate at which a liquid sample flows through a system.

Many processes involve preparation of a liquid sample, flow of the sample along a loading path to a processing device, and flow of the sample through the device. Particularly important devices of this kind are liquid chromatography.(LC) columns, which are widely used to separate, identify, purify and quantify components of mixtures. Other such devices include detectors and reaction chambers. In such processes, reducing the volume of the liquid sample offers important potential benefits. For example, high performance LC (HPLC) typically uses columns 2.0 to 10, e.g. about 4.6, mm in diameter, whereas microcolumn LC (µLC) typically uses columns 2.0 mm or less in diameter and samples having a volume of less than 500 nL. However, as the sample volume decreases, it becomes increasingly difficult to precisely control the volume of the sample and to achieve the square pulse shape of the sample which is desirable. Consequently, systems for preparing and delivering samples to conventional BPLC columns are not satisfactory for use in µLC systems. Attempts have been made to develop injection valves and methods for µLC systems. See, for example, Vissers et al, *J. of Chrom A,* 746, p 1, (1996); Bakalyar et al, *J. Chrom. A,* 762, p 167, (1997); and Foster et al, *J. Chrom. A,* 869, p 231, (2000), and the valves commercially available from VICI Valco Instruments, Rheodyne and Upchurch Scientific. Valve designs include both external and internal sample loops. Injection volumes of less than 100 nL are typically achieved using valves with internal sample loops where a groove in the rotor serves as the loop. Larger injection volumes can be achieved with either internal loops or external loops connected to the valve ports.

SUMMARY OF THE INVENTION

Devices for processing liquid samples are operated at a flow rate which is selected to give satisfactory results in a satisfactory time, and the liquid samples are conventionally prepared and conveyed at the same or a greater flow rate from a sample preparation site to the device. We have discovered, in accordance with the present invention, that improved results are achieved if the sample is prepared and conveyed to the device at a flow rate which is substantially less than the flow rate through the device. The improved results can be attributed to a reduction in the dispersion of the sample, especially as it is prepared at and displaced from the sample preparation site. The low flow rate can also improve the uniformity of multiple samples prepared in the same way.

In a first preferred aspect, this invention provides a method of processing a liquid sample, the method comprising
  (A) causing the sample to flow from a sample preparation site to a processing device, and preferably also causing the sample to flow within the sample preparation site, at a loading rate; and
  (B) causing the sample to flow through the processing device at a processing rate; the loading rate, during at least part of the flow of the sample within the sample preparation site and/or of from the sample preparation site to the device, being substantially less than, preferably less than 0.75 times, e.g. 0.01 to 0.75 times, particularly 0.1 to 0.75 times, the processing rate during at least part of the flow of the sample through the processing device.

In a second preferred aspect, this invention provides apparatus for processing a liquid sample, the apparatus comprising
  (1) a liquid sample preparation site;
  (2) a device for processing the liquid sample;
  (3) a sample loading path from the preparation site to the device; and
  (4) a variable flow rate working fluid supply which is connected to the sample preparation site;

whereby the working fluid supply can be operated to cause the sample to flow through the sample preparation site and from the sample preparation site to the processing device at a loading rate, and to flow through the processing device at a processing rate which is substantially higher than the loading rate.

In a third preferred aspect, this invention provides a method of preparing a liquid sample, the method comprising
  (A) placing a sample composition in a sample reservoir having a working fluid inlet and a sample outlet; and
  (B) supplying a working fluid to the working fluid inlet at a controlled loading rate,
  thus displacing a sample of the sample composition through the sample outlet for a controlled time;

the method having at least one following characteristics
  (1) the controlled loading rate is less than 500 nL/min, e.g. less than 100 nL/min;
  (2) the volume of the sample is less than 100 nL, e.g. less than 50 nL;
  (3) the controlled time is 1-30 seconds, particularly 2-10 seconds, e.g. 2-5 seconds; and
  (4) the sample reservoir is a sample loop in, or associated with, a valve having an actuation time of 60-500, for example 80-200, e.g. about 100, milliseconds.

BRIEF DESCRIPTION OF THE DRAWINGS

The invention is illustrated in the accompanying drawings, which are schematic and not to scale, and in which.

DETAILED DESCRIPTION OF THE INVENTION

Figure 1:
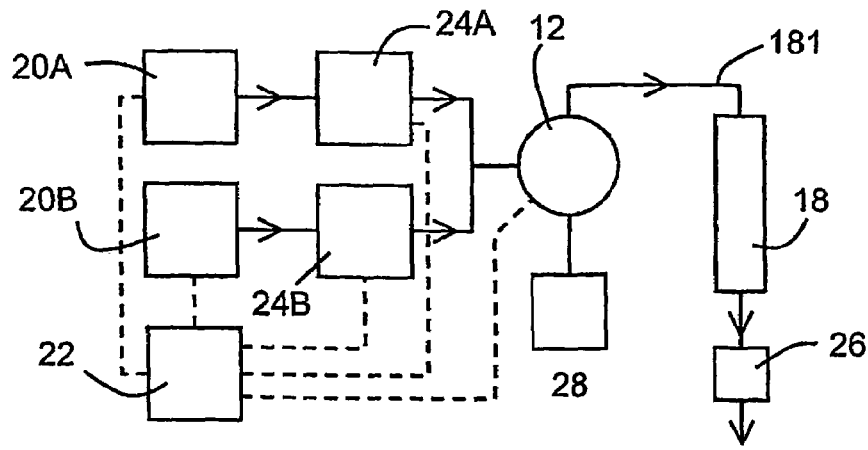
FIGS. 1-3 illustrate an embodiment of the invention.

In the Summary of the Invention above, the Detailed Description of the Invention, the Examples, and the Claims below, and the accompanying drawings, reference is made to particular features of the invention, such features including for example components, ingredients, devices, apparatus, systems, steps and embodiments. It is to be understood that the disclosure of the invention in this specification includes all possible combinations of such particular features. For example, where a particular feature is disclosed in the context of a particular embodiment, a particular Figure, or a particular claim, that feature can also be used, to the extent possible, in the context of other particular embodiments, Figures and claims, and in the invention generally. The invention claimed herein includes the use of features which are not specifically described herein but which provide functions which are the same as, equivalent to, or similar to, features specifically described herein.

The term "comprises" and grammatical equivalents thereof are used herein to mean that other features are optionally present. For example, an apparatus "comprising" (or "which comprises") components A, B and C can contain only components A, B and C, or can contain not only components A, B and C but also one or more other ingredients. Where reference is made herein to a method comprising two or more defined steps, then, unless the context requires otherwise, the defined steps can be carried out in any order or simultaneously, and the method can include one or more other steps which are carried out before any of the defined steps, between two of the defined steps, or after all the defined steps. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. When, in this specification, a range is given as "(a first number) to (a second number)" or "(a first number)-(a second number)", this means a range whose lower limit is the first number and whose upper limit is the second number. For example, "from 8 to 20 carbon atoms" or "8-20 carbon atoms" means a range whose lower limit is 8 carbon atoms, and whose upper limit is 20 carbon atoms. The numbers given herein should be construed with the latitude appropriate to their context and expression. The terms "plural" and "plurality" are used herein to mean two or more.

When reference is made herein to "a", "an", "one" or "the" feature, it is to be understood that, unless the context requires otherwise, there can be one or more than one such feature. When reference is made herein to a first feature and/or a second feature, it is to be understood that unless the context requires otherwise, such terminology is used herein for convenience in identifying such features, and means that either or both features can be present, and that when both features are present, they can be the same or different.

Where reference is made herein to two or more components (or parts or portions etc.), it is to be understood that the components can be, unless the context requires otherwise, separate from each other or integral parts of a single structure or a single component acting as the two or more specified components.

Samples

Any liquid sample can be used in this invention. However, the advantages of the invention are most apparent when the sample has at least one of the following characteristics.

(1) It contains one or more ingredients (known or unknown) which, in the processing device, are separated and/or analyzed and/or reacted.

(2) The volume of the sample is less than 500 nL, for example less than 100 nL, less than 50 nL or less than 10 nL, for example 1.2-43 nL, e.g. 20 nL.

(3) The sample is a nearly ideal, square pulse, sample.

(4) The sample is subject to HBPLC separation with weakly retained compounds, including size exclusion chromatography and other isocratic separations.

The liquid sample can be prepared from a sample source by any method. Many such methods are known. In many known methods, a sample loop or other sample reservoir is filled from a sample source, and a sample of desired size (which may be part or all of the contents of the reservoir) is displaced from the reservoir. The sample can for example be introduced into the reservoir by injecting the sample into the reservoir with a syringe, or by aspirating the sample into the reservoir (e.g. using a syringe to pull a vacuum), or by pumping the sample into the reservoir (for example as part of an on-line monitoring system)

The reservoir can be completely filled or it can be partially filled with a known volume of the sample source. When the reservoir is to be completely filled, the filling is preferably continued until some of the sample source goes to waste, thus ensuring that the reservoir is full. When the reservoir is partially filled, it is preferably filled with a known volume from the sample source in such a way that the sample does not reach the end of the reservoir. Particular methods include the use of valves having internal or external sample loops. Valves in which a groove in a rotor serves as a loop are particularly useful for the preparation of samples having a volume of less than 100 nL. Reference maybe made, for example, to the valves available from Rheodyne, Valco Instruments and Upchurch Scientific, and those described in U.S. Pat. No. 6,290,909 and US Patent Publication No. 2002/0194909, the disclosures of which are incorporated herein by reference.

The sample is preferably driven from the sample reservoir by the pressure of a working fluid which is directed through the reservoir for a time which displaces a sample of the desired volume. Such a timed displacement (also referred to as a moving, temporary or time-slice injection) can for example be accomplished using a pneumatically or electronically actuated valve. If the reservoir has been partially filled with a known volume from the sample source, the whole sample is usually displaced (with some working fluid at each end of the sample). If the reservoir has been completely filled, the volume of the displaced sample is usually less than the volume of the reservoir.

Working Fluids

The sample is preferably driven through the sample preparation site and from the sample preparation site to the processing device, and through the processing device, by the pressure of a working fluid behind the sample. The working fluid is, therefore, one which does not have an adverse effect on the various parts of the apparatus through which it passes. Thus, if the processing device is an LC column, the working fluid is the mobile phase in the LC system.

The working fluid can be a single compound or a mixture of compounds, and can be supplied from a single source or from a plurality of sources supplying the same or different working fluids. When there are a plurality of sources, their outputs can all be combined before any contact with the sample. Alternatively, the working fluid(s) from one or more sources can be used to displace the sample at the loading rate, and the working fluid(s) from one or more further sources can additionally be used to drive the sample at the processing rate. The mixing of working fluids from different sources can be achieved via diffusion or via passive or active devices.

One or more variable flow rate supplies are preferably used to supply the working fluid(s). Preferably, the flow rate supply is continuously variable, can provide flow rates from 1 to 100,000 nL/minute into back pressures of up to 5000 psi (350 kg per cm$^2$) or higher, and has a response time of the order of seconds. Many such supplies are known, for example, direct electrokinetic pumps, electrokinetic flow controllers, electropneumatic pumps with and without hydraulic amplifiers, and mechanically actuated pumps. Reference may be made for example to U.S. Pat. No. 5,942,093 and the documents incorporated herein by reference. Particularly at low flow rates, lead-screw and similar positive displacement pumps may not be satisfactory unless there is active flow rate feedback control. When there is more than one supply, the supplies can be the same or different.

To ensure that the desired flow rate is maintained, information about the working fluid(s), e.g. composition, temperature, pressure, and mixing ratio, can be obtained by flow meters, thermocouples etc. and communicated to a controller which adjusts the variable rate working fluid source(s). In this way, account can be taken of variables such as check valve leakage, pump seal leakage, deformation of mechanical seals, thermal expansion of components, and compression of working fluid(s). Suitable controllers, flow meters, thermocouples etc. are well known. The controller can for example be a PID servo-loop controller, and can include discrete analog and/or digital circuits, a dedicated microprocessor or a programmed computer. The flowmeter can for example be as disclosed in Enoksson et al, J.MEMS, 6, 119-125 (1997), U.S. Pat. No. 6,386,050, or Carvalho et al, Appl. Opt., 33, 6073-7 (1994), the disclosures of which are incorporated herein by reference. The flow meter preferably provides a continuous signal at all the desired flow rates (e.g. 10 to 100,000 nL/min) with a signal bandwidth faster than 1, preferably faster than 10, Hz. A preferred flowmeter comprises a capillary such that the pressure drop across it is at least 5% of the input pressure at the desired flow rate and at least one pressure sensor (preferably a pressure transducer having a volume of less than 10,000 nL) to measure the pressure drop across the capillary.

Processing Devices

The sample can be processed in any device. However the advantages of the invention are most apparent when the device comprises a conduit having an internal diameter of less than 2 mm, for example a µLC column.

Flow Rates

The rate at which the sample flows through the sample preparation site and from the sample preparation site to the processing device is referred to herein as the loading rate. The rate at which the sample flows through the processing device is referred to herein as the processing rate.

We have found that the loading rate while the sample is moving through and out of the sample preparation site (e.g. through a sample loop and an associated valve) often has a greater influence on the dispersion of the sample than the loading rate during subsequent transfer of the sample to the device. This can be attributed to the relative complexity of the flow path of the sample at the preparation site. It is preferred, therefore, that the loading rate should be relatively slow at least until the sample has left the sample preparation site. This may be, for example, for a time of 0.5 to 30 seconds. For optimum results, the relatively slow loading rate should be maintained until just before the sample enters the processing device. This maybe, for example, for an additional time of 0.5 to 30 seconds.

It is, therefore, preferred that, during at least the first part (e.g. at least the first 50%) of the time during which the sample flows through the sample preparation site and from the sample preparation site to the device, the loading rate is less than 0.75 times, e.g. 0.005 to 0.75 times, preferably 0.01 to 0.75 times, e.g. 0.1 to 0.75 times, the processing rate during at least part (e.g. at least 50%) of the time during which the sample flows through the processing device. In many cases, the loading rate is 0.05 to 0.75 times, preferably 0.1 to 0.5 times, the processing rate. Preferably, but not necessarily, at least one of the loading rate and the processing rate is substantially constant.

The time taken to increase the loading rate from a relatively low rate to a rate substantially equal to (within 5% of) the desired processing rate is preferably less than 5 seconds, particularly less than 1 second. The change in flow rate can be gradual or stepwise. The change from the loading rate to the processing rate can be timed or can be triggered, e.g. by an optical, electronic or electrochemical sensor.

In the processing device, e.g. a device comprising a conduit of inner diameter less than 2 mm, the processing rate is typically less than 100,000 nL/min. For example, in an HPLC system, the loading rate is typically 50-500 nL/min, e.g. 100 nL/min, and the processing rate is typically 1,000 to 30,000 nL/min, e.g. 1000 to 15,000 or 3,000 to 4,000 nL/min. By way of example, for a processing device comprising a conduit having an inner diameter of 200-400 micron, the loading rate might be 500-4000 nL/min and the processing rate 4000-30,000 nL/min; and for processing device comprising a conduit having an inner. diameter of 50-200 micron, the loading rate might be 25-500 nL/min and the processing rate 100-4000 nL/min.

Figure 2:
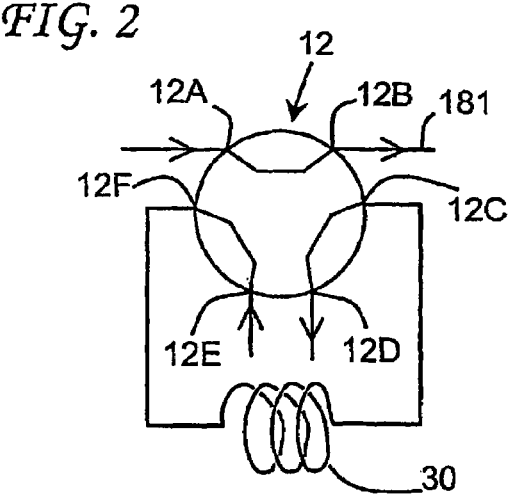
Figure 3:
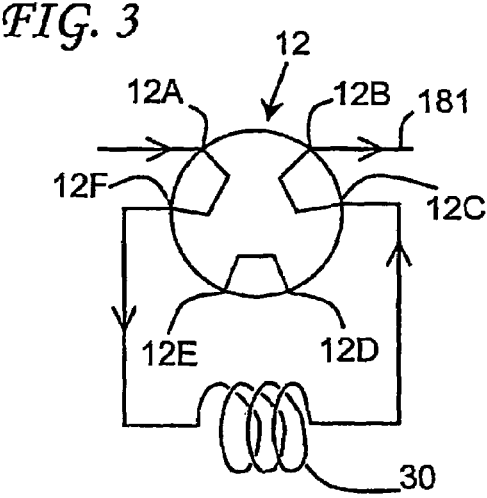

FIGS. 1-3 illustrate one embodiment of the invention. First and second variable flow rate working fluid supplies 20A and 20B supply working fluids at flow rates measured by flow meters 24A and 24B respectively. Rotary valve 12 has six external ports 12A-12F. The outputs of the working fluid supplies are combined and delivered to port 12A. Port 12B is connected via loading conduit 181 to µLC column 18, the output of which flows to detector 26. Ports 12C and 12F are connected to sample loop 30, which can be within the valve or external to the valve as shown in FIGS. 2 and 3. Port 12D is connected to a waste line. Port 12E is connected to sample source 28. A controller 22 controls operation of valve 12 and supplies 20A and 20B, using input from the flow meters, so that the apparatus operates a desired program, as further described below.

The valve 12 can be in a sample injection position (shown in FIG. 2) or in a sample loading position (shown in FIG. 3). In the injection position, a sample previously loaded into the loading conduit 181 is injected into the column 18. Thus, as shown in FIG. 2, (i) ports 12A and 12B are connected, and the combined working fluids drive a sample already present in loading conduit 181 through the column 18 and the detector 26, the sample flowing at the processing rate, and (ii) ports 12E and 12F and ports 12C and 12D are connected so that the sample loop 30 is at least partially filled from the sample source 28.

In the loading position, shown in FIG. 3, ports 12A and 12F are connected, ports 12C and 12B are connected, and ports 12D and 12E are isolated, so that the combined working fluids load a sample from the sample loop into the loading conduit 181 at the loading rate.

EXAMPLES

Example 1

In a set of three experiments, identical samples were displaced from a valve having a 20 nL internal sample loop at fixed flow rates of 3000, 1300 and 540 nL/min respectively.

Figure 4:
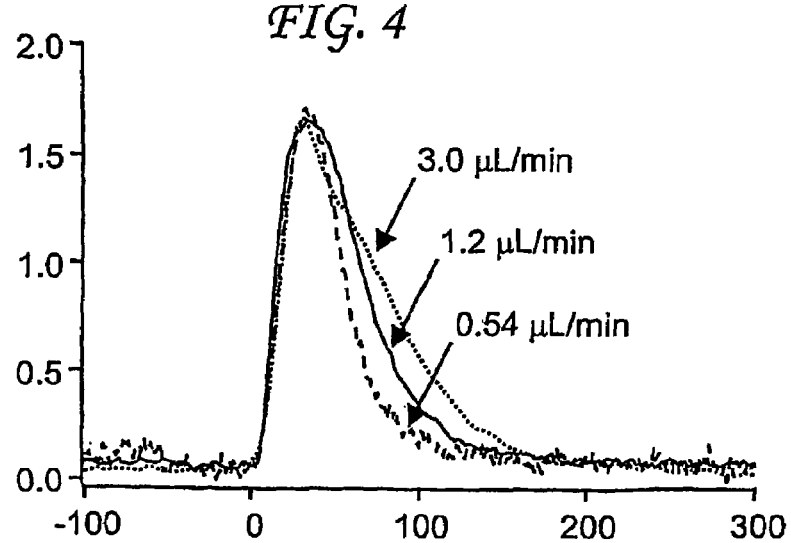
FIGS. 4-6 show the results of the experiments described in Examples 1-3.

The sample composition was a 2 mM solution of thiourea in a 50/50 mixture of methanol and water, and the working fluid was a 50/50 mixture of methanol and water. The absorbance of each displaced sample was measured as it passed through a capillary immediately after leaving the valve. The measured absorbances are shown in FIG. 4, in which the absorbance (in arbitrary units) is on the vertical axis and the volume (in nL) is on the horizontal axis. The calculated variances for the flow rates of 3000, 1300 and 540 nL/min were 1080, 530 and 280 $nL^2$ respectively. These results demonstrate the value of using slow flow rates for displacing samples from a sample preparation sites.

Example 2

Figure 5:
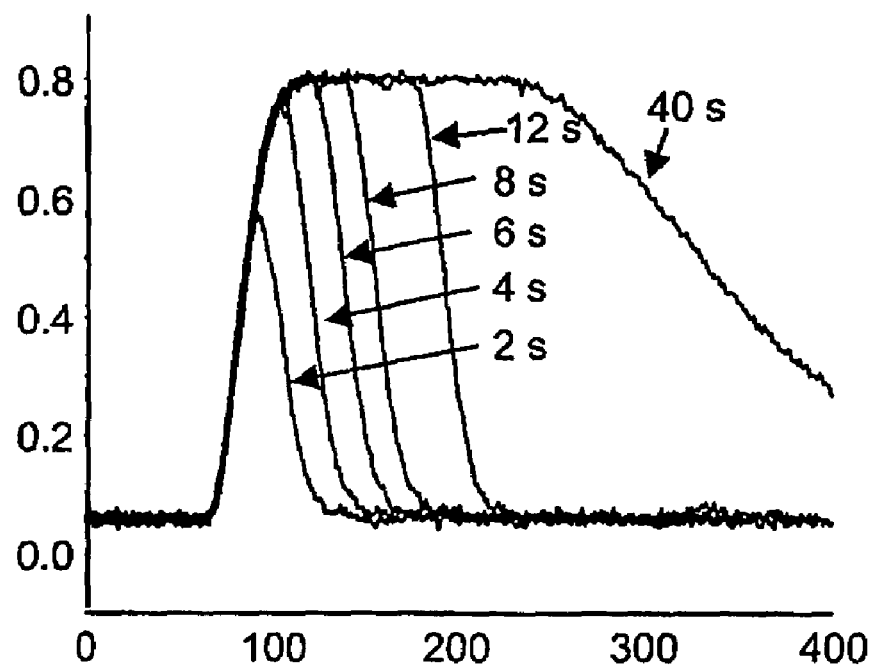

In a set of six experiments, using the same sample material and working fluid as I Example 1, samples were displaced from a valve having a 250 nL internal sample loop at a fixed rate of 540 nL/min over times of 2, 4, 6, 8, 12 and 40 seconds respectively. The absorbance of each displaced sample was measured as it passed through a capillary immediately after leaving the valve. The relative absorbances are shown in FIG. 5, in which the relative absorbance is on the vertical axis and the volume (in nL) is on the horizontal axis. The Full Width Half Maximum widths for the first five samples were 29, 41, 58, 112 and 270 nL respectively. The 40 second injection displaced the entire loop volume, and the result illustrates the dispersive tail from a complete loop injection.

Example 3

Apparatus as illustrated in FIGS. 1-3 was used in this Example. The valve was a Valco CN2 valve with a 250 nL external sample loop and was pneumatically actuated under computer control. The separation column had a length of 150 mm and an internal diameter of 0.3 mm, and was packed with a 3 micron diameter stationary phase (Phenomenax Luna C18). The detector had a volume of about 45 nL and a path length of about 4 mm. The sample was a mixture of uracil, acetophenone, propiophenone and butyrophenone with a buffer of 55% methanol and 45% water. The working fluid in each of the fluid supplies was a 55/45 percent mixture of methanol and water.

Figure 6:
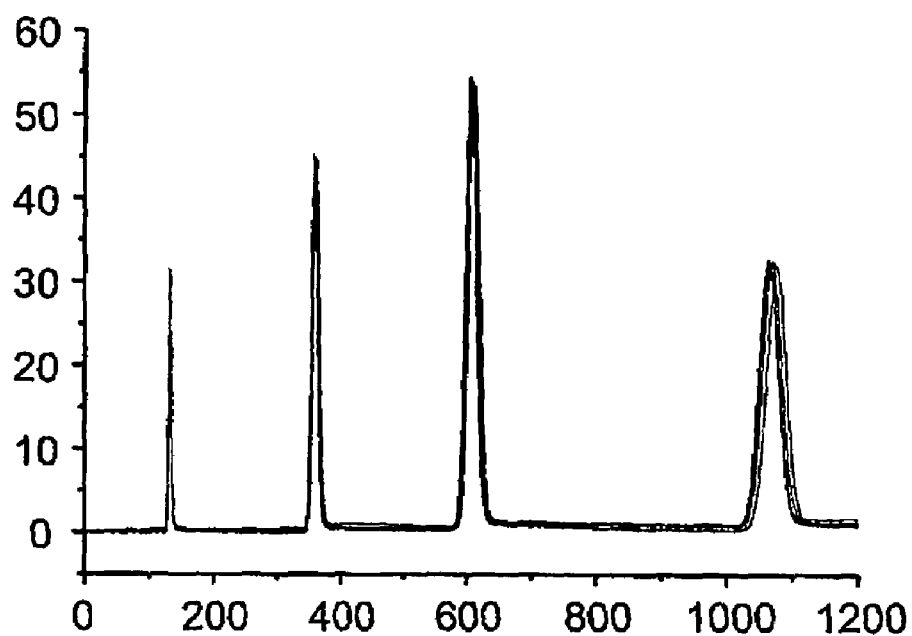

Samples having a volume of 25 nL were displaced over periods of 3 seconds at a flow rate of 500 nL/min, and the flow rate was increased to 4000 nL/min before the samples were injected into the column. The chromatographic results for nine separations are overlaid in FIG. 6, in which the absorbance (in mAU) is on the vertical axis and the time (in seconds) is on the horizontal axis. The relative standard deviation of peak height was less than 1%.

The invention claimed is:

1. A method of processing a liquid sample, the method comprising
    (A) causing the sample to flow within a sample preparation site and from the sample preparation site to a processing device at a loading rate, the sample being prepared in the sample preparation site by displacing a sample of desired size from a reservoir filled from a sample source; and
    (B) causing the sample to flow through the processing device at a processing rate;
the loading rate, during at least part of the flow of the sample within the sample preparation site and from the sample preparation site to the device, being substantially less than the processing rate during at least part of the flow of the sample through the processing device and wherein the processing device is comprises a μLC column having an internal diameter of not more than 2 mm.

2. A method according to claim 1 wherein the loading rate is less than 0.75 times the processing rate.

3. A method according to claim 2 wherein the loading rate is 0.1 to 0.5 times the processing rate.

4. A method according to claim 1 wherein the loading rate during step (A) is substantially constant; the processing rate during step (B) is substantially constant; and there is a rate change period during which the sample flows at a rate which increases from the loading rate to the processing rate and whose duration is less than 5 seconds.

5. A method according to claim 1 wherein the processing rate is less than 100 microliters/minute.

6. A method according to claim 1 wherein the sample has a volume of less than 500 nL.

7. A method according to claim 1 wherein, in steps (A) and (B), the sample is caused to flow by the pressure of a working fluid from a variable flow rate working fluid supply.

* * * * *